United States Patent
Aldalbahi et al.

(10) Patent No.: US 11,001,505 B1
(45) Date of Patent: May 11, 2021

(54) **COPPER OXIDE NANOPARTICLES SYNTHESIZED USING *RHATANY* ROOT EXTRACT**

(71) Applicant: KING SAUD UNIVERSITY, Riyadh (SA)

(72) Inventors: Ali Aldalbahi, Riyadh (SA); Bushra Ibarahim Alabdullah, Riyadh (SA); Manal Ahmed Gasmelseed Awad, Riyadh (SA); Shaykha Mohammed Alzahly, Riyadh (SA); Zainah Ali Alqahtani, Riyadh (SA); Shorouq Mohsen Alsaggaf, Riyadh (SA); Hessa Abdullah Aljasser, Riyadh (SA); Hind Ali Abdullah Alshehri, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/903,183

(22) Filed: Jun. 16, 2020

(51) Int. Cl.
  *C01G 3/02* (2006.01)
  *C01G 3/00* (2006.01)
  *B82Y 40/00* (2011.01)

(52) U.S. Cl.
  CPC ............. *C01G 3/02* (2013.01); *C01G 3/003* (2013.01); *B82Y 40/00* (2013.01); *C01P 2004/64* (2013.01)

(58) Field of Classification Search
  CPC .................................. C01G 3/02; C01G 3/003
  See application file for complete search history.

(56) References Cited

U.S. PATENT DOCUMENTS

| | | |
|---|---|---|
| 2001/0046525 A1 | 11/2001 | Bombardelli et al. |
| 2005/0045031 A1 | 3/2005 | Rajagopalan et al. |
| 2011/0097957 A1 | 4/2011 | Gedanken et al. |

(Continued)

FOREIGN PATENT DOCUMENTS

| | | |
|---|---|---|
| CN | 106530823 A | 4/2017 |
| EP | 2149367 A1 | 2/2010 |
| MX | 2014016072 A | 10/2016 |

OTHER PUBLICATIONS

Bordbar et al., "Green synthesis of copper oxide nanoparticles/clinoptilolite using *Rheum palmatum* L. root extract: high catalytic activity for reduction of 4-nitro pheol, rhodamine B, and methylene blue", Journal of Sol-Gel Science and Technology (2017), vol. 81, pp. 724-733 (Abstract only).

(Continued)

*Primary Examiner* — James A Fiorito
(74) *Attorney, Agent, or Firm* — Nath, Goldberg & Meyer; Richard C. Litman

(57) ABSTRACT

The copper oxide nanoparticles synthesized using *Rhatany* root extract involves preparing the *Rhatany* root extract by adding powdered *Rhatany* roots to boiling water, allowing the mixture to soak overnight, and removing any solid residue by filtering to obtain the aqueous extract. The copper oxide nanoparticles are prepared by mixing equal volumes of the aqueous *Rhatany* root extract and 0.1 M aqueous copper sulfate, heating the mixture at 80° C. for 40 minutes, and adding 1 M sodium hydroxide dropwise to the mixture to precipitate CuO. The precipitate is removed by centrifuge, washed with ethanol, dried, and calcined at 400° C. for 4 hours to obtain the copper oxide nanoparticles. The resulting nanoparticles proved effective in degrading wastewater dyes, showed anticancer activity against human cervical cancer by cell viability assay, and showed antibacterial activity against various strains of bacteria by agar diffusion.

4 Claims, 5 Drawing Sheets

(56) References Cited

U.S. PATENT DOCUMENTS

2015/0208664 A1  7/2015  Borrelli et al.
2016/0302420 A1  10/2016  Gedanken et al.

OTHER PUBLICATIONS

Buazar et al., "Biofabrication of highly pure copper oxide nanoparticles using wheat seed extract and their catalytic activity: A mechanistic approach", Green Processing and Synthesis (2019), vol. 8, Iss. 1.

Singh et al., "Biogenic Synthesis of Copper Oxide Nanoparticles Using Plant Extract and Its Prodigious Potwntial for Photocatalytic Degradation of Dyes", Environ. Res. (2019), vol. 177, doi: 10.1016 (Abstract only).

Tran et al., "Copper Oxide Nanomaterials Prepared by Solution Methods, Some Properties, and Potential Applications: A Brief Review", International Scholarly Research Notions (2014), Article ID 856592, 14 pages.

COPPER OXIDE NANOPARTICLES SYNTHESIZED USING *RHATANY* ROOT EXTRACT

BACKGROUND

1. Field

The disclosure of the present patent application relates to copper oxide nanoparticles, and particularly to copper oxide nanoparticles synthesized using *Rhatany* root extract.

2. Description of the Related Art

Copper oxide nanoparticles (CuO NPs) (and their derivatives, as a type of metal oxide nanoparticles) are widely used in many applications, such as a colorant in many ceramic applications, due to their fair stability, cost-effectiveness and ready availability compared to other expensive noble metals, such as Au, Pt and Ag. In addition to that, other many applications of copper oxide nanoparticles, such as: preparation of slips and glazes, batteries, a catalyst for chemical reactions, solar cells, chemical sensors, an absorbent, a thermal conductivity enhancer, antifouling properties, wastewater treatment, thermal conductivity and anti-oxidation properties, bio-control agents, drug delivery, anticancer activity, and an efficient anti-bacterial agent. However, conventional techniques for preparing copper oxide nanoparticles often employ toxic chemicals, are uneconomical, involve complicated methodology, or are not environmentally friendly. In recent years, there has been increased interest in developing methods of using plant extracts to produce nanoparticles by oxidation or reduction of transition metals or heavy metals. The reduction in size to the nanoparticle scale results in particles having a greater surface area available for reaction, thereby altering properties of the particles and increasing their effectiveness. The use of plant extracts is a "green" approach, which avoids the use of toxic chemicals and is more environmentally friendly, and often more economical. In some cases, it is thought that the use of plant extracts may result in novel composites having different ratios of reduced and oxidized metal or incorporating trace amounts of elements or compounds present in the extract, thereby modifying the crystal structure and properties of the resulting nanoparticles.

Thus, copper oxide nanoparticles synthesized using *Rhatany* root extract solving the aforementioned problems are desired.

SUMMARY

The copper oxide nanoparticles synthesized using *Rhatany* root extract involves preparing the *Rhatany* root extract by adding powdered *Rhatany* roots to boiling water, allowing the mixture to soak overnight, and removing any solid residue by filtering to obtain the aqueous extract. The copper oxide nanoparticles are prepared by mixing equal volumes of the aqueous *Rhatany* root extract and 0.1 M aqueous copper sulfate, heating the mixture at 80° C. for 40 minutes, and adding 1 M sodium hydroxide dropwise to the mixture to precipitate CuO. The precipitate is removed by centrifuge, washed with ethanol, dried, and calcined at 400° C. for 4 hours to obtain the copper oxide nanoparticles. The resulting nanoparticles proved effective in degrading wastewater dyes, showed anticancer activity against human cervical cancer by cell viability assay, and showed antibacterial activity against various strains of bacteria by agar diffusion.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
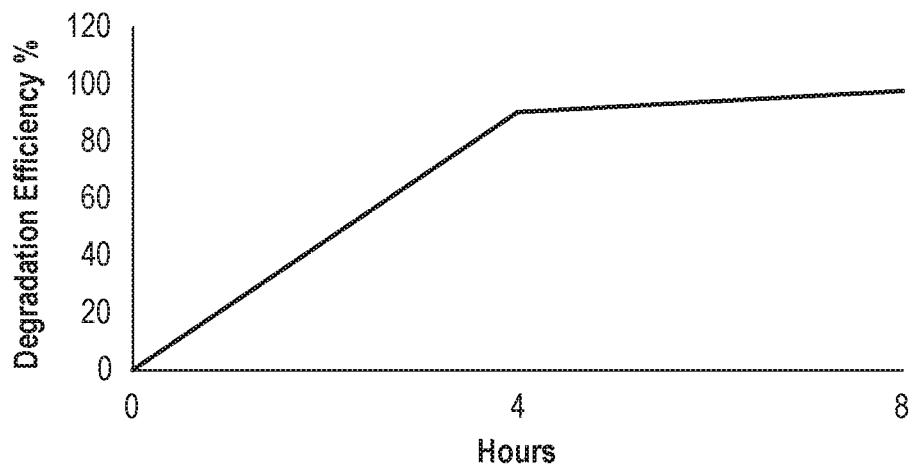
FIG. 1 is a graph of degradation efficiency of the synthesized copper oxide nanoparticles against crystal violet (CV) dye as a function of time.

The copper oxide nanoparticles synthesized using *Rhatany* root extract involves preparing the *Rhatany* root extract by adding powdered *Rhatany* roots to boiling water, allowing the mixture to soak overnight, and removing any solid residue by filtering to obtain the aqueous extract. The copper oxide nanoparticles are prepared by mixing equal volumes of the aqueous *Rhatany* root extract and 0.1 M aqueous copper sulfate, heating the mixture at 80° C. for 40 minutes, and adding 1 M sodium hydroxide dropwise to the mixture to precipitate CuO. The precipitate is removed by centrifuge, washed with ethanol, dried, and calcined at 400° C. for 4 hours to obtain the copper oxide nanoparticles. The resulting nanoparticles proved effective in degrading wastewater dyes, showed anticancer activity against human cervical cancer by cell viability assay, and showed antibacterial activity against various strains of bacteria by agar diffusion.

The following examples show preparation, physical and structural characterization, and testing of the copper oxide nanoparticles for purposes of enablement, and are not intended to be limiting.

Example 1

*Rhatany* Root Extraction

*Rhatany triandra* roots were collected from a spice dealer at the local market in Riyadh, Saudi Arabia, and then were washed several times with tap water, and finally with deionized water. Then, the roots were dried and powdered. To prepared the extract; 10 g of *Rhatany* root powder was added to 100 mL of boiling deionized water and soaked overnight. Then, the aqueous extract was filtered using Whatman filter paper.

Example 2

Synthesis of Copper Oxide Nanoparticles

Approximately 100 ml of copper sulfate (0.1 M) solution was prepared and equal volume of aqueous *Rhatany* roots extract (100 ml) was added, and then the mixed solution was heated in a heating mantle at 80° C. for 40 min, resulting in a red-colored mixture. Drop-wise addition of 1 M NaOH changes the "green" mixture to a brown precipitate, indicating the formation of nanoparticles of water soluble copper oxide. After the color change, the synthesized CuONPs were purified for 20 minutes by centrifugation at 8000 rpm, and then washed with ethanol solvent to remove excess plant compounds and other impurities. After drying at 60° C., the brown powder was then calcined at 400° C. for 4 hours.

Example 3

Copper Oxide Nanoparticles as Catalyst for Photodegradation of Dyes

The photocatalytic property of the synthesized CuONPs was revealed by the potential for degradation of pollutant dyes.

Photocatalytic degradation activity of the synthesized CuO nanoparticles was estimated by the disintegration of crystal violet (CV) and methylene blue (MB) dyes under UV lamp irradiation. For this study, 1 mg $L^{-1}$ of the synthesized CuO nanoparticles was added to 30 mL of CV and MB dye solutions. The photocatalyst samples were dispersed inside the beaker facing UV light at a distance from the lamp (lamp of UV light) under action of a stirrer. Optical absorption spectra were determined upon different light exposure durations using a UV/Vis spectrophotometer in order to monitor the rate of degradation by recording the reduction in absorption intensity of the respective dye at the maximum wavelength. The degradation efficiency (DE) was calculated as in the equation:

$$DE\ \% = (A_0 - A)/A_0 \times 100$$

where $A_0$ is the initial absorption and $A$ is the absorption intensity after photodegradation.

Figure 2:
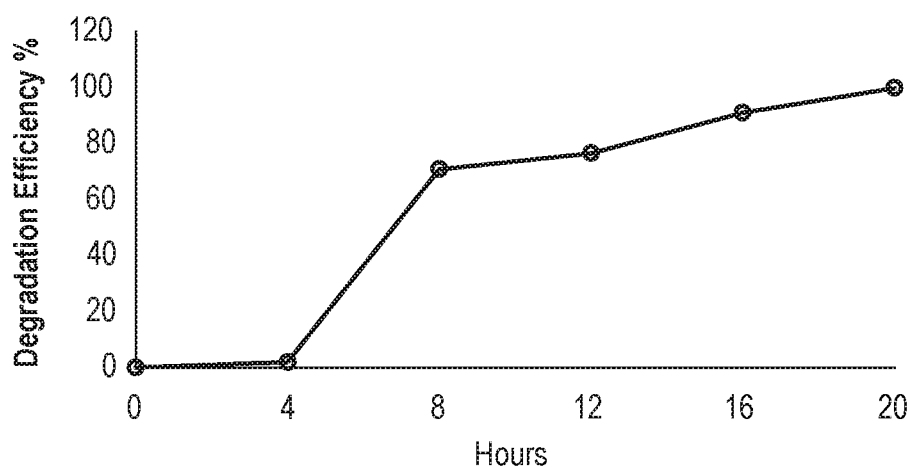
FIG. 2 is a graph of degradation efficiency of the synthesized copper oxide nanoparticles against methylene blue (MB) dye as a function of time.

As expected, the CuONPs catalyst gave a good response under UV irradiation, where the removal % was 97.62% after 8 h under UV irradiation for the CV dye (FIG. 1) and 99.84% after 20 h for MB dye (FIG. 2). The good degradation efficiency for CuO NPs synthesized using *Rhatany* extract opens a wide range of various photocatalytic applications, as well as in water treatment.

Example 4

Cytotoxic Activity of Copper Oxide Nanoparticles Against Cervical Cancer

Figure 3:
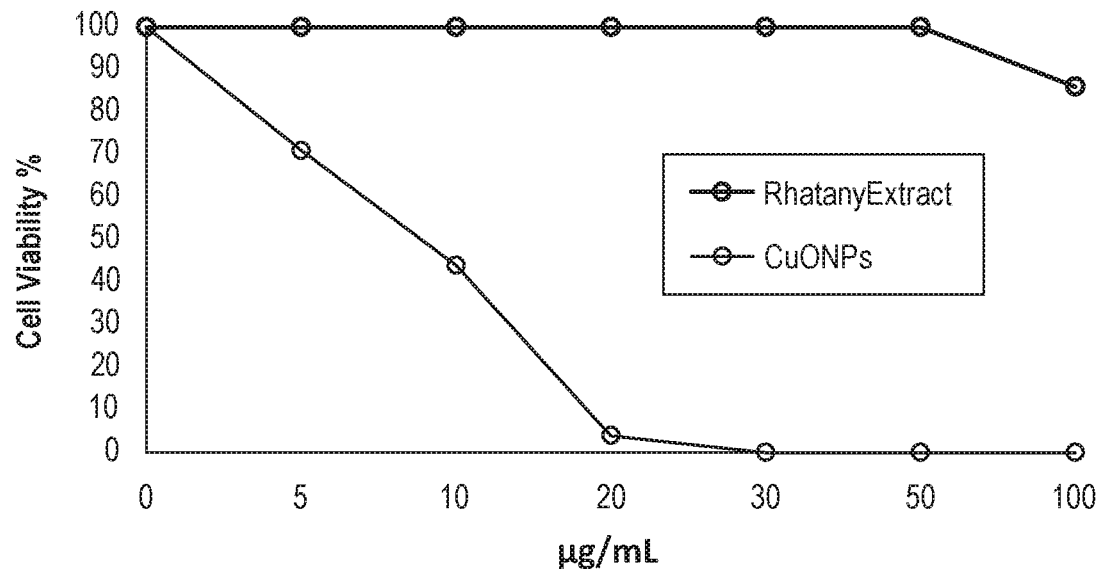
FIG. 3 is a plot comparing cell viability (%) of the human cervical adenocarcinoma cell line (HeLa) as a function of concentration of the synthesized copper oxide nanoparticles to pure aqueous *Rhatany* root extract.

Evaluation of the cytotoxic effects of the resulting CuONPs against a human cervical adenocarcinoma cell line (HeLa) has been determined using viability assay, as shown in FIG. 3. Our results show that the CuONPs, synthesized as described above, have a more cytotoxic effect than pure aqueous *Rhatany* root extract against the Hela cell line.

Example 5

Antibacterial Activity of Copper Oxide Nanoparticles

Figure 4:
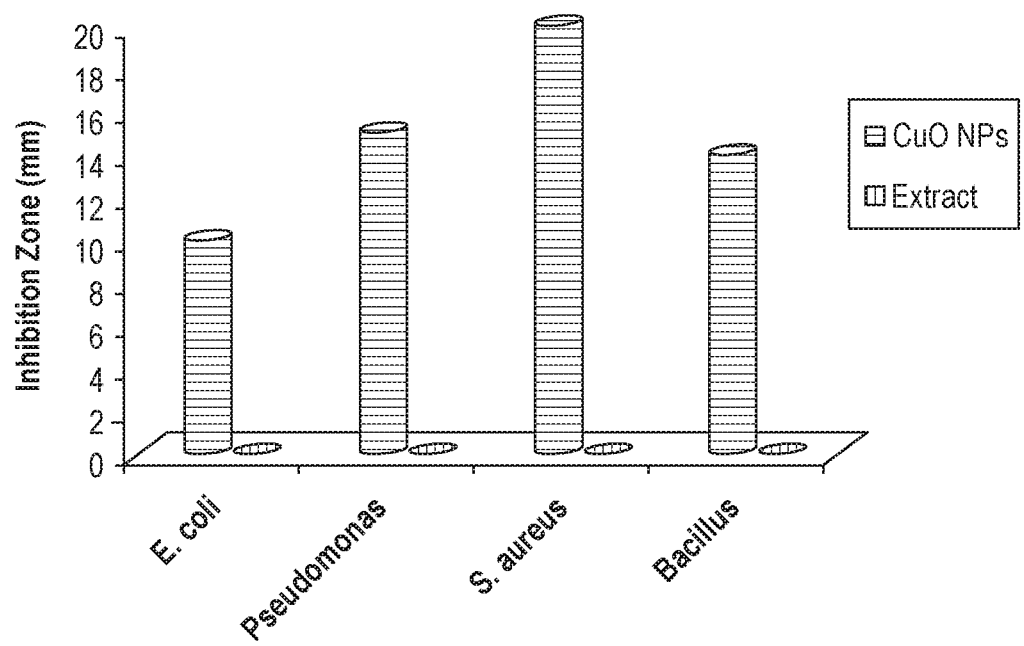
FIG. 4 is a chart showing the size of the inhibition zone in agar well diffusion studies against various species of bacterial pathogens, including *E. coli, Pseudomonas, Staphylococcus aureus*, and *Bacillus*.

In order to analyze the antibacterial activity of CuONPs synthesized by *Rhatany* root extract against most human pathogenic bacteria, the modified agar well diffusion method, microbial style culture collection was used. The antibacterial effects of the NPs are shown in FIG. 4. Our results showed prominent antibacterial activity of CuONPs against all the organisms, while there is no inhibition or antibacterial activity for the pure *Rhatany* root extract.

Example 6

Characterization of the Synthesized Copper Oxide Nanoparticles

Figure 5:
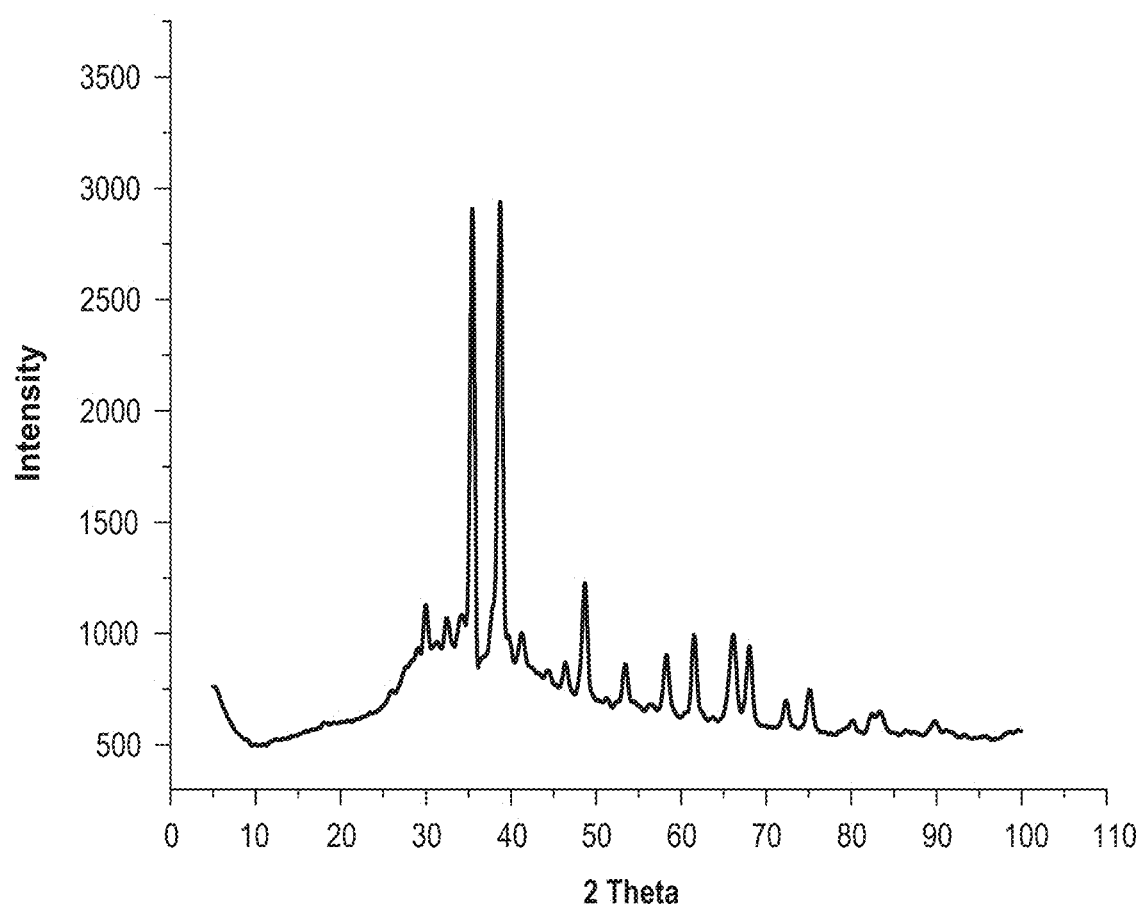
FIG. 5 is an X-ray diffractogram, showing the results of an XRD study of the synthesized copper oxide nanoparticles.

The structural characterization of the resulting CuONPs, synthesized as described above, was carried out by using X-ray diffraction (X'Pert PRO PANalytical). Peaks were indicated for 2θ values at about ≈35°, 38°, and 48°, as presented in FIG. 5, and are assigned to the reflections.

Figure 6A:
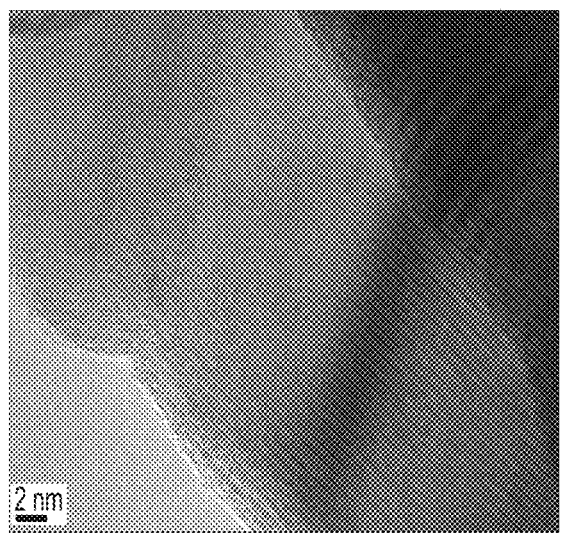
FIGS. 6A and 6B are TEM micrographs of copper oxide nanoparticles synthesized using *Rhatany* root extract.
Figure 6B:
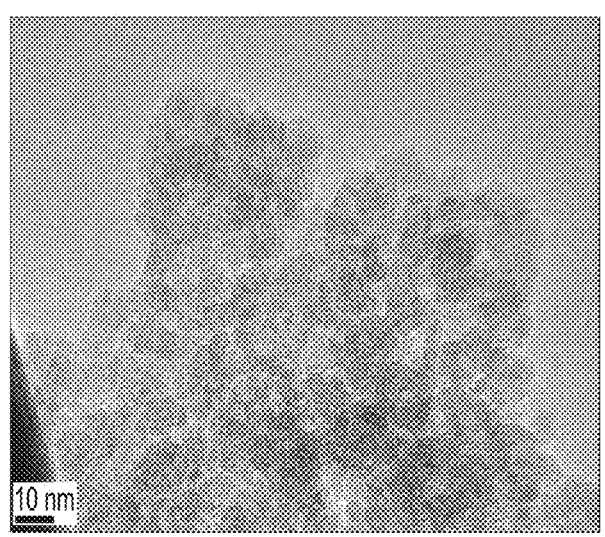
Figure 6C:
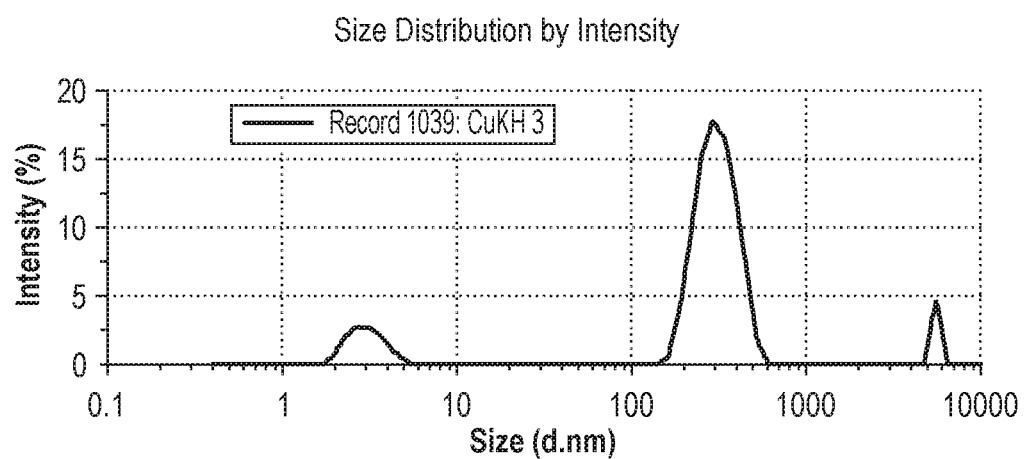
FIG. 6C is a zetasizer plot showing particle size distribution of copper oxide nanoparticles synthesized using *Rhatany* root extract.

TEM research was performed to determine the morphology and size of synthesized CuO NPs. FIGS. 6A and 6B are TEM micrographs showing the synthesized CuO NPs having a semi-spherical shape, with small particle agglomeration appearing as a cluster form. Also, dynamic light scattering (DLS) measurements was performed using a Zetasizer (Nano series, HT Laser, ZEN3600 from Molvern Instrument, UK) to determine the average size of the diameter of the resulting of CuO NPs which was indicated at between 3-500 nm. As shown in FIG. 6C, the CuO nanoparticles are polydisperse with broad size range, varied in size, and showed an agglomeration.

Figure 7:
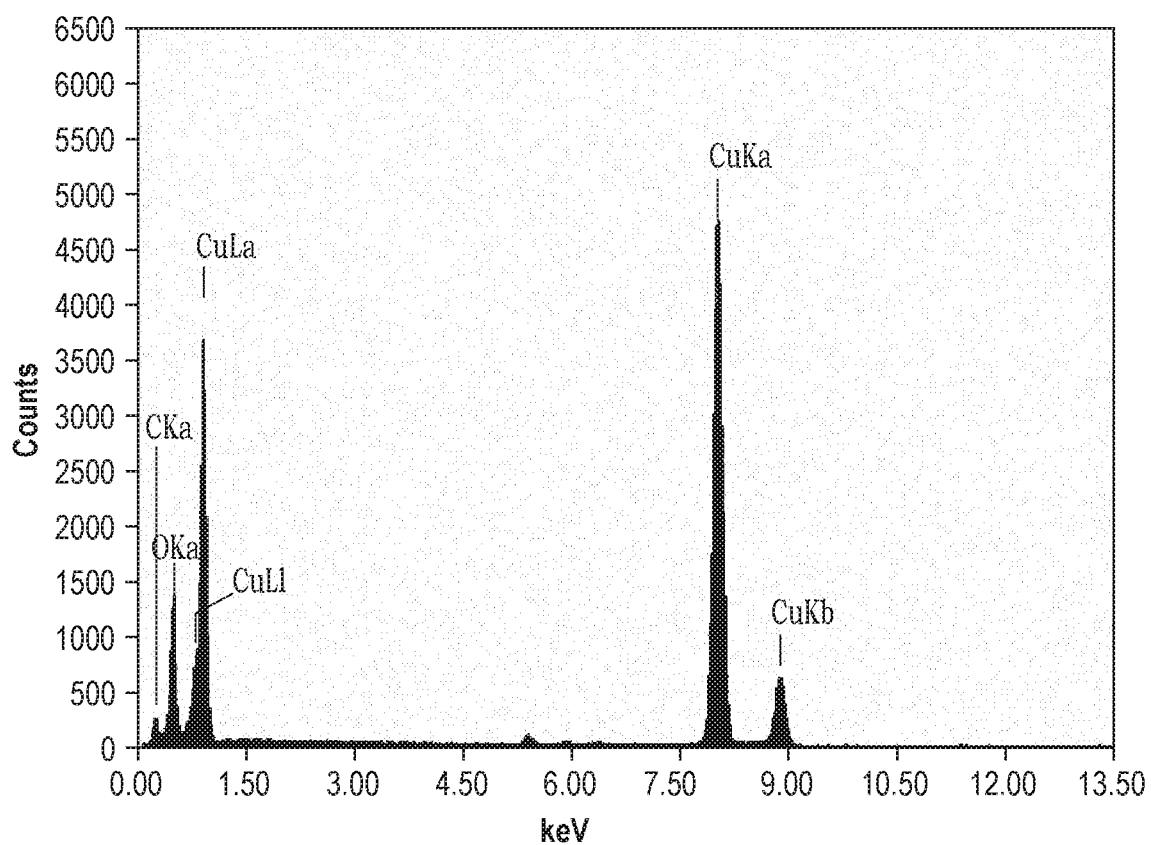
FIG. 7 is the EDX spectrum of copper oxide nanoparticles synthesized using *Rhatany* root extract.

Energy-dispersive X-ray spectroscopy (EDX) was performed to assess the elemental composition of the nanoparticles. The chemical composition of synthesized CuO NPs has been studied by the EDX analysis, as shown in FIG. 7. It has revealed the chemical composition of the synthesized nanoparticles having the elements of Cu and 0. EDX results confirmed that the synthesized CuO NPs using *Rhatany* root extract is uncontaminated pure material.

Figure 8:
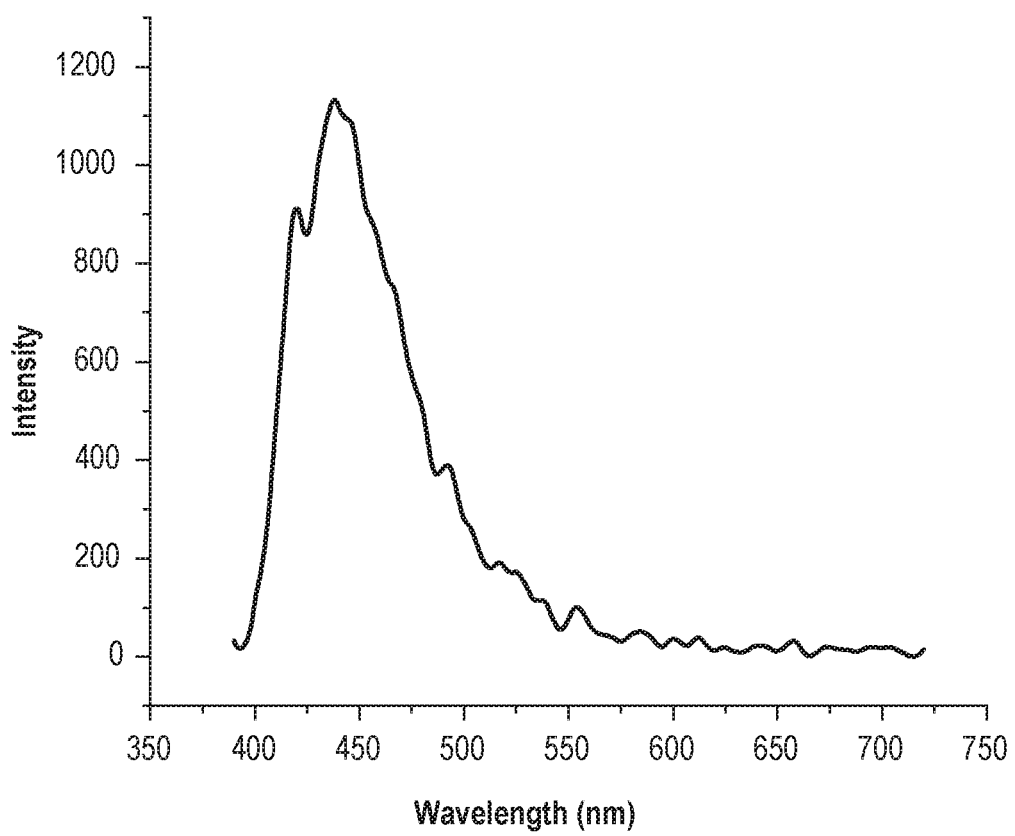
FIG. 8 is the fluorescence UV spectrum of copper oxide nanoparticles synthesized using *Rhatany* root extract.

CuO NPs are reported to exhibit visible photoluminescence (PL). The copper oxide nanoparticles synthesized as described above produced the fluorescent UV spectrum shown in FIG. 8. For an excitation of about 330 nm, the CuO NPs are found to be luminescent with emissions at about 447 nm.

It is to be understood that the copper oxide nanoparticles synthesized using *Rhatany* root extract is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing copper oxide nanoparticles, comprising the steps of:
   mixing equal volumes of an aqueous extract of *Rhatany* root and an aqueous solution of a copper (II) salt;
   heating the mixed volumes at 80° C. for 40 minutes;

adding 1 M sodium hydroxide to the heated mixed volumes dropwise to precipitate copper oxide (CuO) nanoparticles.

2. The method of synthesizing copper oxide nanoparticles according to claim 1, further comprising the steps of:
drying the precipitated nanoparticles; and
calcining the nanoparticles at 400° C.

3. The method of synthesizing copper oxide nanoparticles according to claim 1, wherein the copper (II) salt comprises copper sulfate.

4. The method of synthesizing copper oxide nanoparticles according to claim 1, further comprising wherein the aqueous extract of *Rhatany* root is formed by the steps of:
powdering *Rhatany* roots to obtain *Rhatany* root powder;
adding the *Rhatany* root powder to boiling deionized water to form an extract mixture;
allowing the extract mixture to soak overnight to extract the *Rhatany* roots in water; and
filtering any solid residue to leave the aqueous extract of *Rhatany* root.

* * * * *